US005602265A

United States Patent [19]

van den Kommer et al.

[11] Patent Number: 5,602,265

[45] Date of Patent: Feb. 11, 1997

[54] FRACTIONATION OF TRIGLYCERIDE OILS

[75] Inventors: Marcelle van den Kommer, Gouda, Netherlands; Paul R. Smith, Wellingborough, Great Britain; Adrianus Visser; Cornelis Winkel, both of Maassluis, Netherlands; Deryck Cebula, Bedford, Great Britain

[73] Assignee: Van den Bergh Foods Co., Division of Conopco, Inc., Lisle, Ill.

[21] Appl. No.: 277,536

[22] Filed: Jul. 19, 1994

[30] Foreign Application Priority Data

Jul. 27, 1993 [EP] European Pat. Off. .............. 93305924

[51] Int. Cl.$^6$ ...................................................... C07C 51/43

[52] U.S. Cl. .......................... 554/211; 554/208; 536/127; 526/321

[58] Field of Search ............................ 526/321; 536/127; 554/211, 208

[56] References Cited

U.S. PATENT DOCUMENTS

| | | | |
|---|---|---|---|
| 2,610,915 | 9/1952 | Mattil . | |
| 3,059,005 | 10/1962 | Van de Vusse et al. . | |
| 3,059,008 | 10/1962 | Baur . | |
| 3,059,010 | 10/1962 | Schmid et al. . | |
| 3,059,011 | 10/1962 | Baur . | |
| 3,158,490 | 11/1964 | Baur et al. . | |
| 3,536,461 | 10/1970 | Mueller et al. . | |
| 4,786,415 | 11/1988 | Shibata . | |
| 4,810,787 | 3/1989 | Garvey et al. | 536/127 |
| 4,960,544 | 10/1990 | Van Putte et al. | 554/208 |
| 5,051,408 | 9/1991 | Cooper | 536/127 |

FOREIGN PATENT DOCUMENTS

| | | | |
|---|---|---|---|
| 0081881 | 6/1983 | European Pat. Off. | 554/211 |
| 0188015 | 7/1986 | European Pat. Off. | 554/211 |
| 0535475 | 4/1993 | European Pat. Off. | 554/211 |
| 3514878 | 11/1986 | Germany . | |
| 622735 | 5/1949 | United Kingdom | 554/211 |
| 1015354 | 12/1965 | United Kingdom . | |
| 1282474 | 7/1972 | United Kingdom | 554/208 |

OTHER PUBLICATIONS

Ginstone, H., The Lipid Handbook 1986, pp. 213–215, described on p. 1.
Fette, Seifen, Anstrichmittel, "A Method for the Determination of the Solid Phase Content of Fats Using Pulse Nuclear Magnetic Resonance", 1978, 80 nr. 5 pp. 180–186, described on p. 6 and English equivalent.
Franz, G., "Polysaccharide" § 1.4.2, p. 7.
International Search Report.

*Primary Examiner*—Joseph L. Schofer
*Assistant Examiner*—N. Sarofim
*Attorney, Agent, or Firm*—A. Kate Huffman

[57] ABSTRACT

Process for triglyceride oil fractionation using a crystallisation modifying substance which is i. a copolymer having subunits A and B of which subunit A is derived from maleic acid or itaconic acid and subunit B is derived from vinyl alcohol, alkyl substituted vinyl alcohol, acrylic acid or styrene, A and B being present in a ratio of 10:1 to 1:10, where 5–100% of the the maleic acid or itaconic acid subunits are connected to unbranched (C8–C24)-alkyl chains and where 0–100% of the vinyl alcohol or alkyl substituted vinyl alcohol or acrylic acid subunits are connected to unbranched (C1–C8)-alkyl chains and where ii. inulin or phlein of which 5–100% of the hydroxyl groups on the fructose subunits are connected to (C8–C24) unbranched alkyl chains and 0–95% of the hydroxyl groups have been esterified with a (C1–C8)-alkyl containing fatty acid, preferably acetic acid.

6 Claims, 1 Drawing Sheet

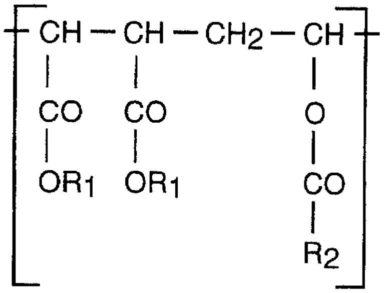
Fig.1.
Fig.2.
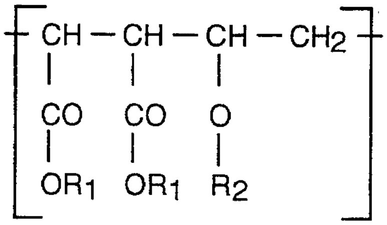
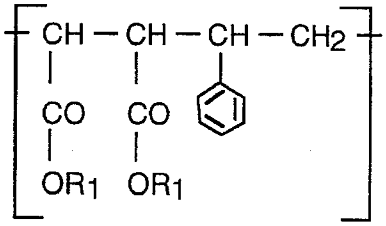
Fig.3.
Fig.4.
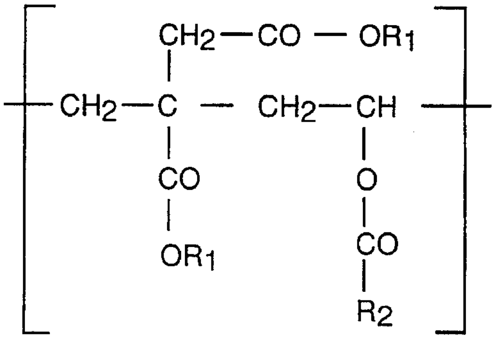

FRACTIONATION OF TRIGLYCERIDE OILS

The present invention is concerned with a process for fractionating triglyceride oils.

The fractionation (fractional crystallisation) of triglyceride oils is described by Gunstone, Harwood and Padley in The Lipid Handbook, 1986 edition, pages 213–215. Generally triglyceride oils are mixtures of various triglycerides having different melting points. Triglyceride oils may be modified e.g. by separating from them by crystallisation a fraction having a different melting point or solubility.

One fractionation method is the so-called dry fractionation process which comprises cooling the oil until a solid phase crystallises and separating the crystallised phase from the liquid phase. The liquid phase is denoted as olein fraction, while the solid phase is denoted as stearin fraction. The separation of the phases is usually carried out by filtration, optionally applying some kind of pressure.

The major problem encountered with phase separation in the dry fractionation process is the inclusion of a lot of liquid olein fraction in the separated stearin fraction. The olein fraction is thereby entrained in the inter- and intracrystal spaces of the crystal mass of the stearin fraction. Therefore the separation of the solid from the liquid fraction is only partial.

The solids content of the stearin fraction is denoted as the separation efficiency. For the dry fractionation of palm oil it seldom surpasses 50 wt. %. This is detrimental to the quality of the stearin as well as the yield of the olein.

For the related solvent fractionation process, where the fat to be fractionated is crystallised from a e.g. hexane or acetone solution, separation efficiencies may be up to 95%.

Dry fractionation is a process which is cheaper and more environmentally friendly than solvent fractionation. For dry fractionation an increase of separation efficiency is therefore much desired.

It is known to interfere with the crystallisation by adding to a crystallising oil a substance which will be generally indicated as crystallisation modifying substance. The presence of small quantities of such a substance in the cooling oil may accelerate, retard or inhibit crystallisation. In certain situations the above substances are more precisely indicated as crystal habit modifiers. Known crystallisation modifiers are e.g. sucrose fatty acid esters, described in U.S. Pat. No. 3,059,010 and fatty acid esters of glucose and derivatives, described in U.S. Pat. No. 3,059,011. These crystallisation modifiers are effective in speeding up the crystallisation rate but are not reported to increase the separation efficiency. They do not even allude to such an effect.

Other crystallisation modifiers, e.g. as described in U.S. Pat. No. 3,158,490 when added to kitchen oils have the effect that solid fat crystallisation is prevented or at least retarded. Other types of crystallisation modifiers, particularly referred to as crystal habit modifiers, are widely used as an ingredient for mineral fuel oils in which waxes are prone to crystallize at low temperatures. U.S. Pat. No. 3,536,461 teaches the addition of a crystal habit modifier to fuel oil with the effect that the cloud point (or pour point) temperature is lowered far enough to prevent crystal precipitation. Or, alternatively, the solids are induced to crystallize in a different habit so that the crystals when formed can pass fuel filters without clogging them.

Other crystal habit modifiers are actually able to change the habit of the crystallized triglyceride fat crystals in a way such that after crystallization the crystals, the stearin phase, can be more effectively separated from the liquid phase, the olein phase. Publications describing such crystal habit modifiers are e.g. GB 1 015 354 or U.S. Pat. No. 2,610,915 where such effect is accomplished by the addition of a small amounts of a polymerisation product of esters of vinyl alcohol or of a substituted vinyl alcohol. U.S. Pat. No. 3,059,008 describes the use of dextrin derivatives for the same purpose. However, these crystallisation modifying substances are still far from ideal. In the former case after three days of crystallization an increase in olein yield from 71% to only 82% was reported. Although such improvement may seem fair, a need exists for more powerful crystallisation modifying substances which act faster and in a dry fractionation environment and which deliver still better improvements in olein yield. The selection of such habit modifiers is a problem, because it is not possible to predict which substances will successfully comply with these requirements.

STATEMENT OF INVENTION

Polymers have been found which are suited as crystallisation modifying substances. In contrast to modifiers of the prior art, the present ones greatly increase the separation efficiency. Accordingly the invention relates to a process employing such modifiers for separating solid fatty material from a triglyceride oil, which comprises the steps A. heating the oil or a solution of the oil in an inert solvent until no longer a substantial amount of solid material is present, B. adding a crystallisation modifying substance to the oil or to the solution of the oil, C. cooling the oil resulting in crystallising a solid stearin phase besides a liquid olein phase and D. recovering the stearin phase by separating it from the olein phase, characterized in that the crystallisation modifying substance is a comb type polymer of the group 1. or 2., where 1. is a copolymer having subunits A and B of which subunit A is derived from maleic acid or iraconic acid and subunit B is derived from vinyl alcohol, alkyl substituted vinyl alcohol, acrylic acid or styrene, A and B being present in a ratio of 10:1 to 1:10, where 5–100% of the the maleic acid or itaconic acid subunits are connected to unbranched (C8–C24)-alkyl chains and where 0–100% of the vinyl alcohol or alkyl substituted vinyl alcohol or acrylic acid subunits are connected to unbranched (C1–C8)-alkyl chains and where
2. is inulin or phlein of which 5–100% of the hydroxyl groups on the fructose subunits are connected to (C8–C24) unbranched alkyl chains and 0–95% of the hydroxyl groups have been esterified with a (C1–C8)-alkyl containing fatty acid, preferably acetic acid.

At microscopic inspection the effect of the presence of such crystallisation modifying substance is that in the oil crystals and crystal aggregates are formed which are conspicuously different from the crystals obtained without crystallisation modifying substance. These crystals and aggregates can be filtered more effectively since the stearin fraction retains less of the olein fraction even at low or moderate filtration pressure. The altered crystallisation results therefore in a considerable increase of the separation efficiency.

The found crystallisation modifying substances belong to a group of polymers having a backbone-chain of which at least a part of the carbon atoms are connected to unbranched (C8–C24)-alkyl side-chains. With respect to the inulin or phlein derivatives the chain is composed of a string of fructose units to which the (C8–C24)-alkyl chains are attached.

The molecular formula of the found crystallisation modifying substance has a comb-shape appearance with "teeth" which may be located at various distances and may have various lengths.

BRIEF DESCRIPTION OF THE DRAWINGS

FIG. 1 illustrates a subgroup of the copolymer of the present invention.

FIG. 2 illustrates a second subgroup of the copolymer of the present invention.

FIG. 3 illustrates a third subgroup of the copolymer of the present invention.

FIG. 4 illustrates a fourth subgroup of the copolymer of the present invention.

DETAILS OF THE INVENTION

The oil to be fractionated is mixed with the crystallisation modifying substance before crystallisation starts, preferably before the oil is heated so that all solid triglyceride fat and preferably also the modifying substance is liquified. Then the oil is cooled to the chosen crystallisation temperature. A suitable crystallisation temperature for e.g. palm oil is 15°–35° C. By choosing a different temperature the composition of the olein and stearin phases may change. Crystallisation proceeds at the chosen temperature until a constant solid phase content is reached. The crystallisation time varies depending on the desired solid phase content. Usual times are in the range of 4–16 hours. During crystallisation the oil may be stirred, e.g. with a gate stirrer. But stagnant crystallisation sometimes gives the best separation efficiency.

For the separation of the solid phase from the liquid phase generally a membrane filter press is used, because it allows rather high pressures. Suitable pressures are 3–50 bar, to be exerted for about 20–200 minutes. However, even with a low or moderate pressure the stearin phase obtained according to the present invention is easily separated from the olein phase. As a rule it takes about 30–60 minutes to have both phases properly separated.

The solids content of the crystal slurry before separation and of the separated stearin phase is measured according to the known pulse NMR method (ref. Fette, Seifen, Anstrichmittel 1978, 80 nr. 5, pp. 180–186).

The characteristic alkyl chains of crystallisation modifying substances of the present invention may be attached to the backbone by reacting a suitable (C8–C24)-alkyl containing alcohol with a carboxyl group or an ether group present on the polymer backbone or on a not yet polymerized subunit or, similarly, a suitable (C1–C8)-alkyl containing carboxylic acid or alcohol with a hydroxyl or carboxyl group present on the polymer backbone or on a not yet polymerized subunit.

As a result, possibly after polymerizing the subunits, the alkyl chains get connected to the polymer backbone via an ether or an ester bridge.

By subjecting the polymer to a pre-treatment with sodium chloroacetate the hydroxyl groups are converted a $—OCH_2C(O)OCH_3$ group which can be converted to an amide with a (C8–C24)-alkyl containing amine $—OCH_2C(O)—NH—$(C8–C24-alkyl).

The alkyl chains attached to the backbone may be the same or different. To the vinyl or acrylic subunit relatively short (C1–C8)-alkyl chains are attached.

The best results have been obtained when the length of the alkyl chains attached to the maleic acid subunit, the itaconic acid subunit or the fructose subunits of inulin or phlein subunits matches the length of the fatty acid chains of the desired stearin phase. Matching occurs when the chains have the same or about the same number of carbon atoms. Therefore, when palm oil is fractionated, preferred alcohols are cetyl (C16) alcohol and stearyl (C18) alcohol.

A more preferred polymer is characterised by copolymer subunits which have been derived from (A) maleic acid and (B) at least one of the group comprising vinyl alcohol, vinyl acetate, methylvinyl ether, ethylvinyl ether and styrene, (A) and (B) being in a ratio of 1:100 to 100:1. The polymer preferably is a repeating dimer composed of a maleic acid subunit and a subunit chosen from the group comprising vinyl alcohol, vinylacetate, methylvinyl ether, ethylvinyl ether and styrene, where 5–100% of the carboxyl groups groups on the maleic acid subunits have been transformed into an ester, ether or amide group connected to an unbranched (C8–C24)-alkyl chain, which chains may be the same or different and where 0–95% of the hydroxyl or carboxyl groups on the vinyl or acrylic subunits have been transformed into an ester, ether or amide group connected to an unbranched (C1–C8)-chain, which chains may be the same or different.

The invention also relates to novel copolymers, suited as crystallisation modifying substance, which is composed of subunits A and B of which subunit A is derived from maleic acid or itaconic acid and subunit B is derived from vinyl alcohol or alkyl substituted vinyl alcohol or acrylic acid, A and B being in a ratio of 10:1 to 1:10 and where 5–100% of the the maleic acid or itaconic acid subunits are connected to unbranched (C8–C24)-alkyl chains and where 0–100% of the vinyl alcohol or alkyl substituted vinyl alcohol or acrylic acid subunits are connected to unbranched (C1–C8)-alkyl chains.

Preferably the alkyl chains are connected to the polymer chain via an ether, an ester or an amide bridge.

A preferred copolymer, suited as crystallisation modifying substance, is composed of subunits A and B of which A is a maleic acid subunit esterified with an unbranched (C8–C24)-alkyl containing alcohol and B is either a styrene subunit or a vinyl alcohol subunit esterified with an unbranched (C1–C8)-alkyl containing fatty acid.

A particularly preferred subgroup of the copolymer of the present invention comprises compounds which are constituted from repeating units according to FIG. 1–4, where $R_1$ is an unbranched C8–C24 alkyl chain and $R_2$ is an unbranched C1–C8 alkyl chain.

Specifically preferred substances are the copolymers poly(dihexadecyl maleate vinyl acetate) and poly(dihexadecyl maleate methylvinyl ether).

The second group of crystallisation modifying substances which are suited for the process of the invention are derivatives of inulin or phlein. Inulin is a polyfructose comprising a terminal glucose subunit where the subunits are mutually connected via a β-1,2 glycosidic linkage. Phlein is a polyfructose comprising a terminal glucose subunit where the subunits are mutually connected via a β2,6 glycosidic linkage. Preferably 5–100% of the hydroxyl groups of the polyfructoses have been esterified with a (C8–C24)-alkyl containing fatty acid, preferably palmitic acid and/or stearic acid, and 0–95% of the hydroxyl groups have been esterified with a (C1–C8)-alkyl containing fatty acid, preferably acetic acid.

A preferred polymer from the previous group is an inulin fraction, having in non-esterified form a molecular weight of 4000–5500 Da, of which per subunit 1.5–3 hydroxyl groups have been esterified with myristic, palmitic acid or stearic acid, while the remaining hydroxyl groups are free or have been esterified with acetic acid.

By fully esterifying inulin with three palmitic acid per subunit molecules the molecular weight increases with a factor 5.5.

A particularly preferred group of crystallisation modifying substances is an inulin fraction, having in non-esterified form a molecular weight of 4000–5500 Da, of which per subunit 1.5–3 hydroxyl groups have been esterified with a mixture of lauric and palmitic acid in a ratio of 9:1 to 1:9. This crystallisation modifying substance is particularly successful in stirred crystallisation.

The process of the invention preferably is carried out as a dry fractionation process, although the invention is useful too for solvent fractionation or detergent fractionation.

The process can be applied on triglyceride oils containing relatively high melting fat such as palm oil, palm kernel oil, shea oil, coconut oil, cottonseed oil, butter oil, hydrogenated rapeseed oil, hydrogenated soybean oil or fractions of these oils or oils obtained from the previous oils by interesterification.

The process is particularly useful for fractionating palm oil. The palm oil might be crude, but generally a refined quality is used.

The crystallisation modifying substance is suitably applied in an amount of 0.005–2 wt. %, preferably 0.01–1 wt. % on the total amount of oil.

The (co)polymers to be used according to the invention can be prepared using common methods for preparing polymers and ethers, esters or amides. The monomers of the subunits are provided with alkyl chains by transferring them into ethers, esters and amides before the polymerisation reaction or, when more appropriate, after the polymerisation step.

A further aspect of the invention is the use of a copolymer composed of subunits A and B, A comprising a maleic acid or itaconic acid subunit esterified with an unbranched (C8–C24)-alkyl alcohol and B comprising either a styrene subunit or a vinyl alcohol subunit or an acrylic acid subunit, the subunits esterified with an unbranched (C1–C8)-alkyl fatty acid as a triglyceride oil crystallisation modifying substance.

The invention comprises in particular the use as a triglyceride oil crystallisation modifying substance of all polymers as defined hereinbefore.

EXAMPLE 1

Dry Fractionation of Palm Oil

Two samples were prepared each containing 1000 g of palm oil (neutralised, bleached, deodorised). The process is carried out as a common dry fractionation process, but to the first sample (A) 1 g (0.1%) of poly(dihexadecyl maleate methylvinyl ether) having an average molecular weight of 164 kDa was added as crystallisation modifying substance, to the second sample (B) no crystallisation modifying substance was added.

Both samples were heated at 70° C. until completely liquefied (no solid fat content) and then cooled in order to crystallise. Crystallisation proceeded under stirring at the chosen temperature of 23° C. for 5 hours until a constant solid phase content was reached. The samples were pressed in a membrane filter for one hour. After filtration the separated fractions were weighted. The olein yield is the weight of the filtrate. The stearin yield is the weight of the crystal mass remaining on the filter. The yields of the measured stearin and olein fractions are given in table I.

TABLE I

| | Sample A 0.1 wt. % modifier | Sample B no modifier |
|---|---|---|
| Temperature/°C. | 23 | 23 |
| Solid phase content slurry/% | 14 | 14 |
| Solid phase content cake/% | 60 | 50 |
| olein yield/% | 77 | 72 |

Before filtration the two samples contained the same amount of solid fat. The comparison shows that the stearin fraction of the crystallisation modifying substance containing sample (A) has retained considerably less olein fraction than sample (B) without a crystallisation modifying substance. The separation efficiency showed a relative increase of 20%.

EXAMPLE 2

Dry Fractionation of Palm Oil

Example 1 was repeated but the crystallisation modifying substance was 1 g (0.1%) of another poly(dihexadecyl maleate methylvinyl ether) having a lower average molecular weight of 80 kDa.

The oil was allowed to crystallise for 16 hours without stirring (stagnant). The fractionation results are given in Table II.

TABLE II

| | Sample A 0.1 wt. % modifier | Sample B no modiifier |
|---|---|---|
| Temperature/°C. | 23 | 23 |
| Solid phase content slurry/% | 12 | 12 |
| Solid phase content cake/% | 54 | 31 |
| Olein yield/% | 78 | 61 |

The separation efficiency showed a relative increase of 74%.

EXAMPLE 3

Dry Fractionation of Palm Oil

Example 1 was repeated but the crystallisation modifying substance was an inulin fraction (0.5%) fully esterified (DS=3) with palmitic acid and having as an ester a molecular weight of 27,000 Da.

The oil was allowed to crystallise for 16 hours without stirring (stagnant). The fractionation results are given in Table III.

TABLE III

| | Sample A 0.5 wt. % modifier | Sample B no modifier |
|---|---|---|
| Temperature/°C. | 23 | 23 |
| Solid phase content slurry/% | 13 | 13 |
| Solid phase content cake/% | 50 | 31 |
| Olein yield/% | 74 | 58 |

The separation efficiency showed a relative increase of 61%.

We claim:

1. A process for separating solid fatty material from a triglyceride oil comprising the steps of:

a. heating the oil or a solution of the oil in an inert solvent until a substantial amount of solid material is no longer present;

b. adding a crystallization modifying substance to the oil or to the solution of the oil;

c. cooling the oil resulting in crystallizing a solid stearin phase besides a liquid olein phase; and d. recovering the stearin phase by separating it from the olein phase, where the crystallization modifying substance is a comb-shaped polymer selected from the group consisting of inulin of which 5–100% of the hydroxyl groups on the fructose subunits are connected to (C8–C24) unbranched alkyl chains and 0–95% of the hydroxyl groups have been esterified with a (C1–C8)-alkyl containing fatty acid.

2. A process according to claim 1, wherein the inulin has a molecular weight of 4000–5500 Daltons of which per subunit 1–3 hydroxyl groups have been esterified with palmitic acid or stearic acid, while the remaining hydroxyl groups are free or have been esterified with acetic acid.

3. Process according to claim 1, wherein the inulin in non-esterified form a molecular weight of 4000–5500 Daltons of which per subunit 1.5–3 hydroxyl groups have been esterified with a mixture of lauric and palmitic acid in a ratio of 9:1 to 1:9, while the remaining hydroxyl groups are free or have been esterified with acetic acid.

4. Process according to claim 1, which is applied as a dry fractionation process.

5. Process according to claim 1, where the triglyceride oil to be fractionated is selected from the group consisting of palm oil, palm kernel oil, shea oil, coconut oil, cottonseed oil, butter oil, hydrogenated rapeseed oil, hydrogenated soybean oil, fractions of these oils and oils obtained from said oils by interesterification.

6. Process according to claim 1, where the crystallisation modifying substance is used in an amount of 0.005–2 wt. % on the total amount of oil.

* * * * *